United States Patent [19]

Mechling

[11] Patent Number: 4,548,289
[45] Date of Patent: Oct. 22, 1985

[54] VARIABLE RESISTANCE TILTBOARD FOR EVALUATION OF BALANCE REACTIONS

[76] Inventor: Richard W. Mechling, 830 Vedado Way, NE., Atlanta, Ga. 30308

[21] Appl. No.: 551,061

[22] Filed: Nov. 14, 1983

[51] Int. Cl.⁴ .............................................. A61B 5/10
[52] U.S. Cl. .................................... 128/774; 128/782
[58] Field of Search ................ 128/774, 782; 272/146, 272/DIG. 6

[56] References Cited

U.S. PATENT DOCUMENTS

| | | |
|---|---|---|
| 3,416,792 | 12/1968 | Morgan et al. |
| 3,605,732 | 9/1971 | Rapoza . |
| 3,702,188 | 11/1972 | Phillips et al. ................ 272/146 X |
| 3,890,958 | 6/1975 | Fisker et al. ................ 128/774 X |
| 3,984,100 | 10/1976 | Firster . |
| 4,183,521 | 1/1980 | Kroeker . |
| 4,270,749 | 6/1981 | Hebern . |
| 4,306,714 | 12/1981 | Loomis et al. |

FOREIGN PATENT DOCUMENTS 825000  4/1981  U.S.S.R. .............................. 128/774

OTHER PUBLICATIONS

Terekhov, "Measuring Mans Stability of Stance", Jrnl. Clin. Eng., vol. 4, No. 1, Jan.–May, 1979, pp. 61–65.
"Construction of a Stabilometer Capable of Indicating the Variability of Non-Level Performance", *Perceptual and Motor Skills*, Dec., 1982.
"Specificity vs. Generality in Learning and Performing Two Large Muscle Tasks", *The Research Quarterly*, vol. 32, No. 1, 1961.
"Body Oscillations in Balancing Due to Segmental Stretch Reflex Activity", *Experimental Brain Research*, 1980.

*Primary Examiner*—Edward M. Coven
*Attorney, Agent, or Firm*—Jones & Askew

[57] ABSTRACT

A method and apparatus for the objective analysis of human balance reactions involving a pivotable platform and a variably positionable viscous damping device which provides a known resistance to angular displacement of the platform. Parameters of movement of the platform such as differential weight and angular velocity for varying resistances are recorded as a measure of the subject's balance and motor skills.

22 Claims, 5 Drawing Figures

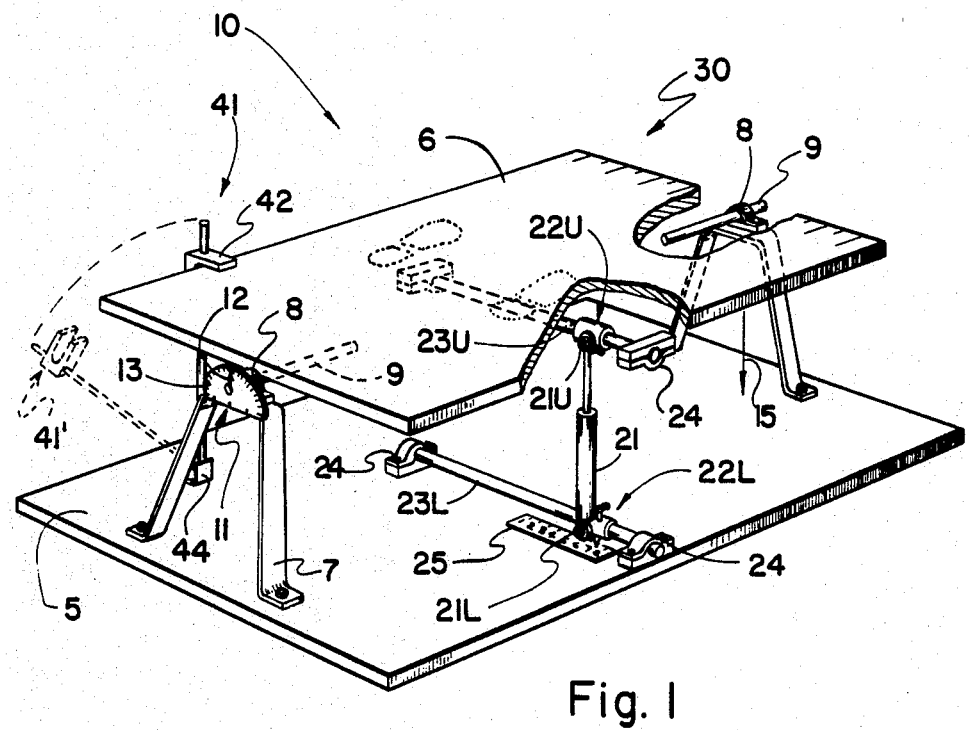
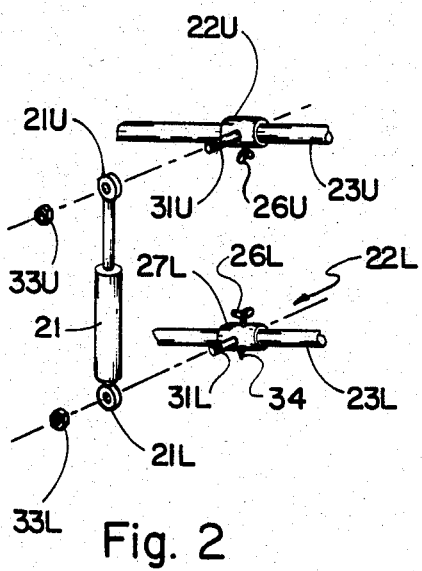
Fig. 2
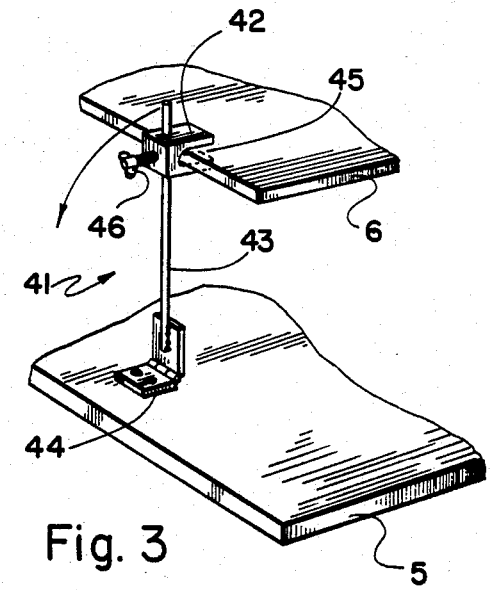
Fig. 3

VARIABLE RESISTANCE TILTBOARD FOR EVALUATION OF BALANCE REACTIONS

FIELD OF THE INVENTION

The present invention relates generally to evaluating human balance reactions, and relates more specifically to a tiltboard having selectively variable stability, and a method for objectively observing a person's balance reactions.

DESCRIPTION OF THE PRIOR ART

The phenomenon of balance is an extremely intricate process which involves sensory input from a variety of sources including visual, muscle tensions, skin pressure, and inner ear sensations. In general, the act of balancing for a biped such as a human involves the movement of one's center of gravity away from a base of support. As the movement of the center of gravity occurs, receptors such as skin pressure receptors and proprioceptive muscle tension receptors in the support limbs sense the weight moving over the body limbs in a particular direction. Additionally, the optical system detects the tilting of the visual field, and the otoliths of the inner ear detect the movement of the head away from vertical. All of these sensory inputs combine with central nervous system sensory interpretation in order to provide central nervous system instructions to particular muscles in the frame to effectuate balance recovery. The accuracy of these sensory inputs are important determinants to the speed and skillfulness of balance and therefore the efficacy of postural maintenance.

In the treatment of individuals affected by brain damage, inner ear disorders, or other physical conditions affecting balance, there is a need for objective observation and analysis of balance reactions so that progress or regress in the particular physical condition can be evaluated. Prior to the present invention, the available techniques for objectively evaluating complex balance motions left much to be desired.

One apparatus which has been used to evaluate muscle coordination or skill and motor learning ability is the stabilometer, described in Bachman, "Specificity vs. Generality in Learning and Performing Two Large Muscle Motor Tasks," *The Research Quarterly*, Vol. 32, No. 1, 1961. This apparatus generally consists of a horizontally pivoted board upon which a subject stands erect, with the feet generally a foot or so apart and straddling a supporting axle. The center of rotation in such an apparatus is placed approximately ten inches higher than the board upon which the subject stands. The low position of the board relative to the axis of rotation presumably eases the balancing test conducted. Motion of the stabilometer is measured with a work adder. Any movement of the board is recorded on a flat disk which carries a calibrated dial scaled in arbitrary units, each unit generally representing about twelve degrees of platform tilting. Microswitches fastened under each end of the tilting board and wired in series with an electric clock ensure that all movement is recorded only when the subject has the board completely out of balance as opposed to at rest against a baseboard and can thereby rest without movement.

One problem with the stabilometer approach to evaluation of balance skills is that due to the free movement of the board, persons with severe balance disorders are unable to perform the balance test. There is great diversity in the levels of impairment to balance that can occur with the many types of nerve injury and disfunction. This requires an evaluation tool that can be set to a level of challenge to balance that exactly matches a patient's abilities. The stabilometer or tiltboard does not offer a wide spectrum of difficulty settings. Therefore, it is impossible with such a conventional stabilometer to compensate for varying degrees of disability or balance abnormality.

More recently, researchers have attempted to provide a quantitative score sensitive to variability of balance performance for use with a stabilometer. Accordingly, there has been proposed a stabilometer which measures balance when the subject is level and still and, in addition, cumulatively penalizes the quantitative score of balance performance when the balance platform is held in a nonhorizontal position. This proposed stabilometer, described in Murray, "Construction of a Stabilometer Capable of Indicating the Variability of Non-Level Performance," *Perceptual and Motor Skills*, December, 1982, includes an integrator system which provides a cumulative account of varying voltages that correspond linearly with the extent of error made when the platform moves from the non-error horizontal position. Although such an apparatus is an admirable attempt to objectivize the evaluation of balance and motor skills, this proposed stabilometer suffers from the same disadvantage as the original stabilometer, namely, that the apparatus, being loose and providing only one setting of a small resistance to movements of the person on the platform, is unusable with persons having severe balance disorders, who cannot easily and safely mount or use the device so that his balance skills can be evaluated.

SUMMARY OF THE INVENTION

Briefly described, the present invention provides an improved stabilometer or tiltboard which allows the objective analysis of human balance reactions and which provides a selectable predetermined resistance to movement of the platform relative to the base. Additionally, the preferred embodiment of the present invention includes measuring means associated with the platform and the base which allows measurement and recordation of a parameter of movement of the platform relative to the base as a person attempts to balance. Advantageously, the preferred embodiment further includes an adjustment feature which allows for varying the amount of the predetermined resistance to movement of the platform. This feature allows varying degrees of resistance to be imparted to the stabilometer or tiltboard, so that persons having differing degrees of balancing disorders or disabilities can mount the stabilometer and perform a balancing test that can be adjusted until the difficulty level matches the person's level of skill. The resistance can be made extremely stiff, so that severely balance-handicapped individuals can stand upon the board and use their limited balance reactions to work at the task of maitaining a horizontal board position. As the individual progresses in his or her rehabilitation, the resistance to movement can be decreased, making the balancing more demanding, and thereby providing challenges which encourage, promote, and quantify rehabilitation.

In the preferred embodiment, the variable resistance to movement is provided by a viscuous damping device in the form of a conventional automotive shock absorber that may be variably positioned from the axis of rotation of the platform inwardly and outwardly of the axis. There is also provided a clamp or stabilizer assembly which allows the platform to be positioned and locked at a predetermined angular orientation from which the patient attempts righting back to the horizontal when the clamp is unlocked. This provides additional degrees of challenge for persons whose balance skills are being rehabilitated. The stabilizer assembly is also used to immobilize the tiltboard for mounting.

The present invention also facilitates an improved method of objectively evaluating human balance reactions. This method comprises the steps of providing a known, predetermined resistance to the angular displacement of the stabilometer, situating a person whose balance reactions are to be evaluated on the stabilometer, and recording a movement parameter of the stabilometer produced by the person's reactions to the stabilometer. In a preferred method, the movement parameter of the stabilometer which is recorded is the angular displacement of the stabilometer. By further recording the time of such angular displacement, the movement can be measured in degrees of an arc per second. This angular velocity can be converted into other useful parameters of movement such as the differential weight on opposite sides of the axis, which is a measure of the shift of the subject's center of gravity.

Inasmuch as the resistance to movement can be varied, this movement parameter can be recorded for a particular individual having a severe balance disability and then the stabilometer can be set to a "looser" or lower resistance to movement for a person having a slighter balance disability and thereafter the balance reactions of this person can be recorded. Advantageous, therefore, the method and apparatus disclosed herein allows the assessment of the balance capabilities of persons with varying degrees of balance disability, as well as the objective quantification of balance movements in response to different degrees of resistance, so that a chart of the progress or regress of the individual's rehabilitation can be prepared.

Accordingly, it is an object of the present invention to provide an improved stabilometer for the objective analysis of human balance reactions.

It is another object of the present invention to provide an apparatus for the analysis of human balance reactions which provides a resistance to movement so that persons having varying degrees of balance disability can be evaluated.

It is another object of the present invention to provide an apparatus for the analysis of human balance reactions which provides a variable predetermined resistance to movement so that progress or regress of balance and motor skill disabilities can be objectively evaluated and recorded.

It is another object of the present invention to provide an apparatus for the objective analysis of human balance reactions which employs a movable platform which can be immobilized at a predetermined angular position so as to provide for ease in mounting and a different balance skill test.

It is another object of the present invention to provide a method for the objective evaluation of human balance reactions involving the provision of a known predetermined resistance to the angular displacement of a stabilometer, and the measurement of a movement parameter of the stabilometer produced by the person's reactions to the resistance provided by the stabilometer.

These and other objects, features, and advantages of the present invention may be more clearly understood and appreciated from a review of the following detailed description of the preferred embodiment and by reference to the appended drawings and claims.

BRIEF DESCRIPTION OF THE DRAWINGS

FIG. 1 is a perspective view of a preferred embodiment of the present invention.

FIG. 2 is a perspective exploded view of the variably positionable shock absorber assembly employed in the embodiment shown in FIG. 1.

FIG. 3 is a perspective view of the platform stabilizer assembly employed in the embodiment shown in FIG. 1.

DETAILED DESCRIPTION OF THE PREFERRED EMBODIMENT

Figure 4:
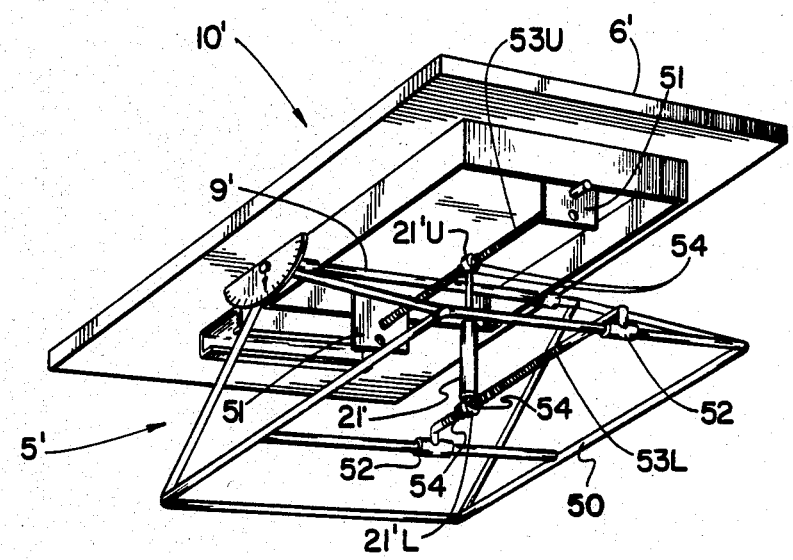
FIG. 4 is a bottom perspective view of a second preferred embodiment.

Referring now to the drawings, in which like numbers indicate like elements throughout the several views, FIG. 1 shows a preferred embodiment of a variable resistance tiltboard 10 constructed in accordance with the present invention. The tiltboard 10 is pivotably mounted to and supported above a portable but relatively stationary rectangular planar base unit 5.

The tiltboard 10 further comprises a rectangular planar platform 6 pivotally supported above base 5 by means of support brackets 7 affixed to platform 6. The support brackets 7 include bearings 8, which permit rotation of shaft 9 affixed to platform 6. Shaft 9 is aligned with the intended axis of rotation of platform 6 relative to the base 5.

A rotation indicator 1, which indicates the amount of rotation of shaft 9, and correspondingly the degree of tilt of platform 6, is mounted to one of brackets 7. The rotation indicator 11 comprises a needle 12 affixed to the end of shaft 9 and indicates the degrees of rotation on a protractor 13, which is rigidly affixed to bracket 7. It will thus be appreciated that the rotation indicator 11 gives an objective reading of the degree of tilt of platform 6 by observing the alignment of needle 12 with protractor 13. Although in the preferred embodiment the needle 12 is freely movable with respect to protractor 13, it should be understood that a conventional peak-reading needle which stops at the highest inclination can be employed to record the degree of movement. Also, it is preferable to employ a needle and protractor which is easily readable so that the amount of rotation in a predetermined time period (as measured with a stopwatch or other timing means) can be measured for computing angular velocity, for reasons discussed more fully below.

A conventional automotive shock absorber 21 is employed in the preferred embodiment to provide a predetermined resistance to tilting of the platform 6. Additionally, the shock absorber 21 is selectively positionable inwardly and outwardly of the axis of rotation so as to allow variation in the amount of resistance to tilting. The upper and lower ends 21U and 21L, respectively, of shock absorber 21 are attached to upper and lower sliding collar assemblies 22U and 22L, respectively, which in turn slide along upper and lower mounting bars 23U and 23L, respectively. Upper bar 23U is rigidly affixed to the underside of platform 6 by means of mounting brackets 24U. The longitudinal axis of upper mounting bar 23U is oriented substantially perpendicular to the axis of rotation of platform 6.

Similarly, lower mounting bar 23L is rigidly affixed to the top surface of base 5 by means of mounting brackets 24L. The longitudinal axis of lower mounting bar 23L is oriented substantially perpendicular to the axis of rotation of platform 6, and is also substantially parallel to the longitudinal axis of upper bar 23U. A stability indicator scale 25 is located adjacent along to and along the sliding path of lower sliding collar assembly 22L for purposes of indicating the relative stability of the platform 6 as the position of the shock absorber 21 is varied.

FIG. 2 shows more particularly the upper and lower sliding collar assemblies 22U and 22L. The sliding collar assemblies comprise tubular upper and lower sliding collars 27U and 27L, respectively, which receive and slide along upper and lower mounting bars 23U and 23L, respectively. Setscrews 26U and 27U releasably fasten the sliding collars to the mounting bars.

The upper and lower ends 21U and 21L, respectively, of shock absorber 21 are affixed to upper and lower sliding collars 27U and 27L, respectively, by means of threaded shoulder studs 31U and 31L on the collars. The shoulder studs 31U, 31L extend at right angles from the sliding collars, and receive nuts 33U and 33L, respectively, which hold the shock absorber ends. A position indicator 34 is attached to the underside of the lower sliding collar 27L for indicating the position of shock absorber relative to stability indicator scale 25.

It will now be understood that movement of the shock absorber inwardly and outwardly of the axis of rotation of the platform 6 varies the amount of resistance of movement. Movement inwardly decreases the resistance, while movement outwardly increases the resistance. Preferably, shock absorber 21 comprises a 50/50 valved shock absorber which requires equal force to extend as well as collapse the shock absorber. It should be understood that other similar devices can be employed to provide constant resistance to rotation, such as a viscous damping device. It should also be understood that such resistance devices preferably provide resistance which is proportional to and in the opposite direction of the instantaneous velocity vector (indicated at 15 in FIG. 1) of the movement of the platform.

It will be understood that changing the distance between the damping force provided by shock absorber 21 (against which the tilting platform 6 moves) and the axis of rotation changes the length of the lever arm through which the force acts. Accordingly, changing the distance results in quantifiable changes in the "steadiness" of the platform 6. This steadiness may be quantified (and calibrated) by placing a known weight a known distance from the axis of rotation. A position scale 30 is provided on the upper surface of the platform 6 for measuring the distance from the axis, and may also be used for measuring placement of a person's feet or body on the platform. Placing the known weight at the known distance causes the platform to move at a predetermined angular velocity, which can be measured in radians or degrees per second, or in inches per second of the edge of the platform. By repeating the measurement of angular velocity for the known weight and distance for various positions of the shock absorber 21, the tiltboard 10 can be calibrated and known values representing relative steadiness can be recorded.

The measure of comparative steadiness in the preferred embodiment is angular velocity per foot pound, or degrees per second per foot pound. Thus, for calibration, placing the known weight at a known distance from the shaft will produce a given angular velocity. Conversely, an observed angular velocity (obtained for example by observing the amount of tilt during one second) can be converted into an amount of force in foot pounds. Since the subject's foot position will be known and prerecorded, this force can be converted into the weight shifted by the subject over the limb, and this weight shift (i.e. the shift of the center of gravity) can be recorded as a parameter of balance.

In other words, the steadiness of the tiltboard can be expressed in the difference in foot pounds, for each side of the axis of rotation, required to move the platform at a given angular velocity or degrees of an arc per second. This differential weight in foot pounds on one side of the axis and the angular velocity with which the platform tilts in response to the shifting weight of a subject are both objective parameters of tiltboard movement which are useful in analyzing and assessing balance reactions.

Stated in still other terms, during calibration the known weight and distance of shock absorber 21 from the shaft 9 produces a given angular velocity. When a test subject who is off-balance responds to the tiltboard movement, a higher (or lower) angular velocity may be observed as the subject shifts his or her weight. This observed angular velocity can be directly recorded as a parameter of movement of the platform, or can be converted by a simple calculation into a differential weight in foot pounds and recorded as a parameter of movement. Although the computations are slightly more complex if the subject's feet are not equally spaced from the pivot axis of shaft 9, it will be understood that the same parameters of movement can be observed and recorded for this type of subject placement as well.

The preferred embodiment of the present invention also comprises a stabilizer assembly 41 which is used to lock and immobilize the platform 6 while a person mounts or dismounts. Preferably, the stabilizer assembly 41 is height-adjustable so that the platform 6 can be locked at varying angular inclinations, so as to provide for testing of balance reactions at varying initial inclinations. As best shown in FIG. 3., the the stabilizer assembly 41 comprises a platform grasping block 42 slidably mounted on an upright rod 43, which is pivotably mounted by means of a hinge 44 to base 5. The surface of grasping block 42 defines a slot 45 of sufficient width to readily accept the thickness of platform 6. The grasping block 42 is releasably and adjustably affixed to the upright rod 43 by means of setscrew 46. By moving the grasping block upwardly or downwardly along the rod 43 and fastening with setscrew 46, the grasping block may be positioned to hold the platform 6 immobile at a predetermined angular inclination. In order to release the platform for a balancing test, after a subject has mounted the platform, the grasping block is manually pulled or kicked out of engagement with the platform 6, releasing the platform to pivot.

In normal use of the apparatus, the position of the shock absorber 21 is first preset by loosening setscrews 26U and 26L, positioning the shock absorber and collar position indicator 34 along stability indicator scale 25, and tightening setscrews 26U and 26L when the desired position is reached. The indicated position along the scale 25 is the length of the lever arm from the shaft 9, and is used in calculating the force resistive of movement. It should be appreciated that a second collar position indicator could be incorporated into the upper sliding collar assembly 22U which, accompanied with the corresponding stability indicator scale 25, would minimize possible error due to possible misalignment of the shock absorber.

The person whose balance is to be evaluated then mounts platform 6 with the stabilizer assembly 41 engaged with the platform. Foot or hand positioning for the subject is then selected by means of position scale 30, and recorded. The stabilizer assembly 41 is then uncoupled from the platform 6, and the person's balance reactions are analyzed with the aid of rotation indicator 11 for a predetermined interval of time. Readings from rotation indicator 11 can be coupled with the "relative stability setting" obtained from stability indicator scale 25 as well as the hand or foot positioning data obtained from position scale 30 to obtain results useful in determining a person's balance reactions.

FIG. 4 illustrates a second embodiment 10' employing a base assembly 5' constructed of tubular members 50 which pivotably support the platform 6' on shaft 9'. Brackets 51, 52 support parallel threaded rods 53U, 53L, which are received in the eyelets 21'U, 21'L of the shock absorber 21'. Four threaded nuts 54 allow the shock absorber 21' to be variably positioned along the threaded rods 53U, 53L to provide variable resistance.

The simplest use for the apparatus is by placing the subject whose balance is to be evaluated in a standing position with the feet straddling the shaft 9, with each foot being equidistant from the shaft. However, it should be understood that many uses for the apparatus will occur to those skilled in the art. For example, certain persons having severe balance disorders may be unable to assume or hold a standing position without constant assistance. Progress for such persons can be measured with the present invention by placing the persons in a plantigrade position, or other lower developmental position such as a "all-fours" position on hands and knees with the axis of the body aligned with the shaft. Alternatively, the person can assume the all-fours position with the hands on one side of the axis and the feet on the opposite side of the axis. Thus, it will be understood that various developmental positions for subjects can be employed and measurements of the response made and recorded. As in the case for persons who can stand on the board, varying amounts of resistance can be employed as progress in developing balance is made, beginning with the greatest amount of resistance should the situation require the same.

As another example, persons whose balance skills are highly developed can also be evaluated by placing them on the platform 6 with very small amounts of resistance, almost to the point that the board is freely pivotable. Such persons can also be evaluated by placing the person's feet at known positions with respect to the shaft 9 which are not equidistant from the shaft, for example, having the left foot one and a half feet to the right of the shaft and the right foot six inches to the left of the shaft.

Figure 5:
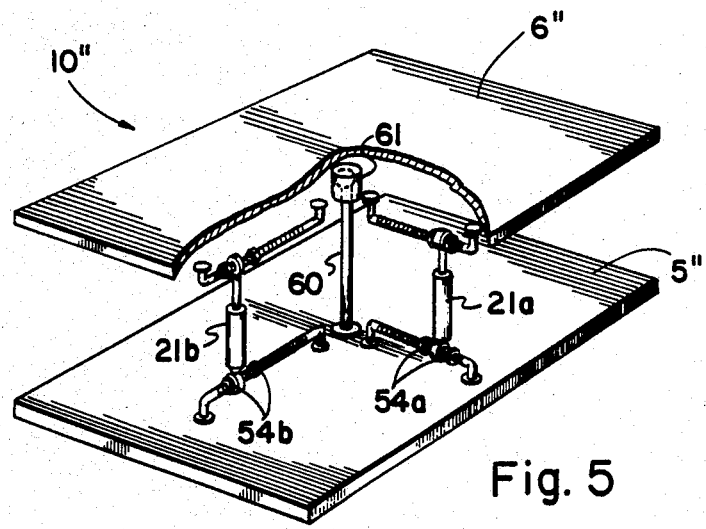
FIG. 5 is perspective view of a third embodiment having multiple degrees of freedom.

It should also be understood that the apparatus described above can be easily modified to provide more than one degree of freedom. FIG. 5 illustrates an embodiment 10" wherein the platform 6" possesses three degrees of freedom and wherein a second shock absorber assembly 21b mounted on base 5" orthogonal to the first shock absorber assembly 21a resists the angular movement of the platform 6" in a second direction. A single support rod 60 rigidly mounted to the base 5" supports the platform 6" via a ball-and-socket joint 61, such that forward and backward, as well as left and right, movement is possible. The shock absorber assemblies 21a, 21b are separately positionable with respect to the support rod 60 so that the resistances to movement may be separately varied.

As another example, by treating the base 5 as another platform similar to the platform 6, and by supporting the base 5 along a second shaft (not shown) oriented perpendicularly to the shaft 9, and supporting the base 5 for movement about this perpendicular second shaft with a second shock absorber, an apparatus having three degrees of freedom can also be constructed so as to provide varying amounts of resistance to tilting of the platform 6 in any direction.

It will be understood that persons having severely impaired balance reactions will tend to have a large sway or variation in placement of their center of gravity. A large shift of the center of gravity will cause a large amount of body weight to be placed over a particular limb, and the skin pressure receptors and muscle tension receptors in this limb will then respond with an increased quantity of nerve impulses indicative of the large displacement of the center of gravity. Accordingly it is preferable for persons having such severely disordered balance reactions to be provided with a large amount of resistive force so that they are able to maintain posture on the platform. In this situation, the platform 6 tilts very slowly in response to the large shift of body weight so that the person can maintain posture on the board by having more time to process and react to a large quantity of nerve impulses from the skin pressure receptors and the muscle tension receptors. This also allows a relatively long period for central processing of the inputs from the optical system (from visual field tilting) and the inner ear, so that the impaired nervous system has time to respond.

As another example of the use of the present invention in evaluating the severity of balance impairement, the subject can be placed on the platform 6 at a given resistance, and this resistance varied until the physical therapist observes subjectively that the subject is unable to maintain posture or balance. The point at which difficulty is encountered in maintaining posture or balance can be recorded as an objective measure or parameter of movement of the balance disability and recorded as a baseline from which to measure progress or regress in development of recouperation of the balance skills. For example, the therapist could record an observation such as that the patient stands on the tiltboard set at 50 foot poundds for 15 seconds without tilting greater than five degrees in either direction. In such a situation, the therapist's objective would be to have the patient or subject approach a zero angular velocity, wherein there is very little perceptible tilting of the platform 6.

The preferred embodiment of the present invention has been disclosed by way of example and it will be understood that other modifications may occur to those skilled in the art without departing from the scope and the spirit of the appended claims.

I claim:

1. An apparatus for the objective analysis and quantification of human balance reactions, comprising:
   a base;
   a platform pivotably supported above said base for supporting a person whose balance reactions are to be analyzed;

variable resistance means operatively associated with said platform and said base for providing a selectively variable predetermined resistance to the movement of said platform relative to said base; and measuring means operatively associated with said platform and said base for measurement of a parameter of the movement of said platform relative to said base so as to obtain an objective quantification of a person's balancing ability.

2. The apparatus as described in claim 1, wherein said variable resistance means comprises viscous damping means.

3. The apparatus as described in claim 1, wherein the resistance to movement of said platform relative to said base is directly proportional to and in the opposite direction of the instantaneous velocity of said platform relative to said base.

4. The apparatus as described in claim 3, wherein the proportionality of resistance to movement of said platform relative to said base is variable.

5. The apparatus as described in claim 1, wherein said variable resistance means comprises a conventional automotive shock absorber having a longitudinal axis oriented substantially perpendicular to an axis of rotation of said platform relative to said base, said shock absorber being mounted between and having opposite ends attached to said platform and said base.

6. The apparatus as decribed in claim 5, wherein said shock absorber is variably positionable with respect to said axis of rotation of said platform relative to said base.

7. The apparatus as described in claim 5, further comprising a second conventional automotive shock absorber having a longitudinal axis oriented substantially perpendicular to a second axis of rotation of said platform relative to said base, said shock absorber being mounted between and having opposite ends attached to said platform and said base.

8. The apparatus as described in claim 1, further comprising means for immobilizing said platform at a predetermined angular position relative to said base.

9. The apparatus as described in claim 8, wherein said immobilizing means is operative to release said platform from said predetermined position to allow movement.

10. The apparatus as described in claim 1, wherein said variable resistance means comprises means for resisting angular movement of said platform relative to said base.

11. The apparatus as described in claim 1, wherein said variable resistance means comprises resisting means selectively positionable with respect to an axis of rotation of said platform relative to said base.

12. A method of objectively evaluating the balance reactions of a subject, comprising the steps of:

selecting a predetermined resistance to displacement of a movable platform to match the subject's level of balance skill;

situating the subject on the platform;

allowing the subject to attempt to maintain balance on the platform; and recording a movement parameter of the platform produced by the subject's reactions to the platform so as to obtain an objective quantification of the subject's balancing ability.

13. The method of claim 12, wherein the person is situated in a standing position.

14. The method of claim 13, further comprising the step of situating the feet of the person on the platform at predetermined positions with respect to an axis of angular displacement of the platform.

15. The method of claim 12, wherein the person is situated on hands and knees.

16. The method of claim 12, further comprising the steps of:

providing a second predetermined resistance to the displacement of the platform; and recording a second movement parameter of the platform produced by the person's reactions to the platform.

17. The method of claim 12, further comprising the steps of providing a predetermined displacement for the platform prior to the step of situating the person on the platform, and releasing the platform from the predetermined displacement prior to recording the movement parameter.

18. The method of claim 12, wherein the step of recording a movement parameter of the platform comprises determining the relative displacement of the platform, and recording the determined relative displacement.

19. The method of claim 12, wherein the step of recording a movement parameter of the platform comprises determining the angular velocity of the platform, and recording the determined angular velocity.

20. The method of claim 12, wherein the step of recording a movement parameter of the platform comprises determining the differential weight shifted by the person over a given body limb in response to movement of the platform, and recording the differential weight.

21. The method of claim 11, wherein said predetermined resistance is an initial predetermined resistance, and further comprising the step of decreasing said initial predetermined resistance to provide a lower, second predetermined resistance for a subject demonstrating improved or progressive balance skills relative to said initial predetermined resistance.

22. The method of claim 11, wherein said predetermined resistance is an initial predetermined resistance, and further comprising the step of increasing said initial predetermined resistance to provide a higher, second predetermined resistance for a subject demonstrating handicapped or regressive balance skills relative to said initial predetermined resistance.

* * * * *